US006720341B2

(12) United States Patent
Moriyama et al.

(10) Patent No.: US 6,720,341 B2
(45) Date of Patent: Apr. 13, 2004

(54) PREVENTIVES/REMEDIES FOR KIDNEY DISEASES

(75) Inventors: Toshiki Moriyama, Minoh (JP); Enyu Imai, Takarazuka (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/240,174

(22) PCT Filed: Feb. 28, 2001

(86) PCT No.: PCT/JP01/01531

§ 371 (c)(1), (2), (4) Date: Oct. 17, 2002

(87) PCT Pub. No.: WO01/74391

PCT Pub. Date: Oct. 11, 2001

(65) Prior Publication Data

US 2003/0096843 A1 May 22, 2003

(30) Foreign Application Priority Data

Mar. 31, 2000 (JP) ........................................ 2000-97258

(51) Int. Cl.[7] ............................................ A61K 31/445

(52) U.S. Cl. ....................... 514/352; 514/241; 514/242; 514/243; 514/245; 514/256; 514/258; 514/275; 514/300; 514/303

(58) Field of Search ................................ 514/241, 242, 514/352, 243, 245, 246, 256, 258, 275, 300, 303

(56) References Cited

U.S. PATENT DOCUMENTS

| | | | |
|---|---|---|---|
| 5,478,838 A | 12/1995 | Arita et al. | 514/300 |
| 6,218,410 B1 * | 4/2001 | Uehata et al. | 514/352 |

FOREIGN PATENT DOCUMENTS

| | | |
|---|---|---|
| EP | 641781 | 3/1995 |
| JP | 10-113187 | 5/1998 |
| JP | 10-201480 | 8/1998 |
| WO | 98/06433 | 2/1998 |

OTHER PUBLICATIONS

Katsuyuki Nagatoya et al., "Rock Sogaizai Y27632 ni yoru Jinkanshitsu Senika Yokusei Koka no Kento", Nippon Jinzo Gakkai, Dai 43 kai Nippon Jinzo Gakkai Gakujutsu Soukai, Mar. 1, 2001.

Takashi Fujimoto et al., "Saibou Secchaku oyobi Kokkaku to Jin Shikkan—Tei Bunshiryl GTP Ketsugo Tanpakushitsu Rho ni yoru Saibou Kokkaku to Secchaku no Seigyo Kiko wo Chuushin ni—", Nippon Naika Gakkai Zasshi, vol. 88, No. 1, pp. 148–154, 1999.

M. Amano et al., "Formation of Actin Stress Fibers and Focal Adhesions Enhanced by Rho–Kinase", Science, 275, pp. 1308–1311, 1997.

Katsuyuki Nagatoya et al., "Rock Sogaizai Y27632 ni yoru Jinkanshitsu Senika Yokusei Koka no Kento", Nippon Jinzo Gakkaishi, vol. 42, No. 3, (Gakujutsu Soukai Go), p. 181, Apr. 2000.

Katsuyuki Nagatoya et al., Nippon Jinzo Gakkai, Dai 43 kai Nippon Jinzo Gakkai Gakujutsu Soukai, Mar. 1, 2001 & English translation thereof.

Katsuyuki Nagatoya et al., Nippon Jinzo Gakkaishi, 42(3) (Gakujutsu Soukai Go), p. 181 (0–157) (Apr., 2000) & English translation thereof.

* cited by examiner

*Primary Examiner*—James H Reamer
(74) *Attorney, Agent, or Firm*—Wenderoth, Lind & Ponack, L.L.P.

(57) ABSTRACT

A compound having a Rho kinase inhibitory activity, such as (+)-trans-4-(1-aminoethyl)-1-(4-pyridylcarbamoyl)-cyclohexane, has a renal interstitial fibrosis inhibitory action in renal interstitial fibrosis model mice and various other actions, and therefore, is useful as an agent for the prophylaxis or treatment of renal diseases.

6 Claims, 1 Drawing Sheet

PREVENTIVES/REMEDIES FOR KIDNEY DISEASES

This application is a U.S. national stage of PCT/JP01/01531 filed Feb. 28, 2001.

TECHNICAL FIELD

The present invention relates to an agent for the prophylaxis or treatment of renal diseases, which comprises a compound having a Rho kinase inhibitory activity.

BACKGROUND ART

Renal diseases include a disease wherein hematuria and proteinuria are developed by various causes, and a disease wherein kidney function becomes low to develop acute or chronic renal failure that requires dialysis as the occasion demands. Many renal diseases are difficult to treat and prognosis is poor, and not a small number thereof proceed to terminal renal failure. In addition, renal diseases tend to increase with aging, where marked increase in the number of dialysis patients and aging of dialysis patients pose a significant medical and therapeutic problem of renal diseases.

In recent years, any progressive renal diseases including glomerulonephritis are said to show, in the course of developing a terminal renal failure, a significant disease state with concomitant fibrosis of renal interstitium, (*Igaku no ayumi*, Vol. 190 No. 1, 1999). Furthermore, many researchers have pointed out a clear correlation between interstitial fibrosis lesion obtained from the renal biopsy tissue of glomerulonephritis patients, and renal function or prognosis.

Accordingly, renal fibrosis has drawing attention as a universal treatment target for a renal disease that resists treatment.

At present, various investigations of the mechanism of glomerular inflammation causing interstitial inflammations, and further fibrosis are ongoing. It is considered that tubular epithelial cells are activated by a high urinary protein, components contained therein, such as a complement, a lipoprotein and ferritin, and inflammatory cytokines (IL-1$\beta$, TNF-$\alpha$ etc.) produced and released in glomerulus, and the epithelial cells themselves produce cell adhesion molecules such as chemokine (e.g., MCP-1, RANTES etc.), integrin, VCAM-1, ICAM-1, selectin, osteopontin and the like to promote cellular infiltration. The infiltrated monocyte and T lymphocyte secrete new cytokines that act on tubular epithelial cells and infiltrated cells. Fibroblast is considered to be involved in such inflammatory lesion. In addition, cells having the characteristics of blood vessel smooth muscle, which is called myofibroblast (myoFb), are occasionally found. It is postulated that, in such interstitial lesion, extracellular matrices, such as type I and type III collagen, fibronectin and proteoglycan, are accumulated along with the destruction and atrophy of existent structures, and cell loss occurs due to apoptosis, which completes a renal fibrosis lesion.

On the other hand, as a compound having a Rho kinase inhibitory activity, a compound of the formula (I) to be mentioned later has been reported (WO98/06433). Certain isoquinolinesulfonamide derivative and isoquinoline derivative are also reported to show a Rho kinase inhibitory activity (WO98/06433 and Naunyn-Schmiedeberg's Archives of Pharmacology 385(1) Suppl., R219, 1998). Furthermore, it has been reported that ethacrynic acid, certain vinyl benzene derivatives such as 4-[2-(2,3,4,5,6-pentafluorophenyl)-acryloyl]cinnamic acid and the like and cinnamic acid derivative have a Rho kinase inhibitory activity (WO00/57914, JP-A-2000-44513).

The pharmaceutical use of a compound having a Rho kinase inhibitory activity is disclosed in WO98/06433, and described to be widely useful as a therapeutic agent of hypertension, a therapeutic agent of angina pectoris, a cerebrovascular spasm suppressant, a therapeutic agent of asthma, a therapeutic agent of peripheral circulatory disturbance, a premature delivery preventive, a therapeutic agent of arterial sclerosis, an anticancer drug, an anti-inflammatory agent, an immunosuppressant, a therapeutic agent of autoimmune diseases, an anti-AIDS agent, a therapeutic agent of osteoporosis, a therapeutic agent of retinopathy, a cerebral function improver, a contraceptive drug, and a gastrointestinal tract infection preventive.

Furthermore, the compound of formula (I) has been already known to be useful as an agent for the prophylaxis or treatment of disorders of circulatory organs such as coronary, cerebral, renal, peripheral artery and the like (e.g., a therapeutic agent of hypertension, a therapeutic agent of angina pectoris, a therapeutic agent of renal and peripheral circulation disorder, a suppressive agent of cerebrovascular contraction and the like), which is potent and long lasting, and also as a therapeutic agent of asthma (JP-A-62-89679, JP-A-3-218356, JP-A-4-273821, JP-A-5-194401, JP-A-6-41080 and WO95/28387).

The isoquinolinesulfonamide derivative described in the above-mentioned WO98/06433 is known to be effective as a vasodilating agent, a therapeutic agent of hypertension, a cerebral function improver, an anti-asthma agent, a heart protecting agent, a platelet aggregation inhibitor, a therapeutic agent of neurologic manifestation, an anti-inflammatory agent, an agent for the prevention and treatment of hyperviscosity syndrome, a therapeutic agent of glaucoma, a diminished tension agent, a motor paralysis improver of cerebral thrombosis, an agent for prevention and treatment of virus infection and transcriptional control factor inhibitor (JP-A-57-200366, JP-A-61-227581, JP-A-2-256617, JP-A-4-264030, JP-A-6-56668, JP-A-6-80569, JP-A-6-293643, JP-A-7-41424, JP-A-7-277979, WO97/23222, JP-A-9-227381, JP-A-10-45598 and JP-A-10-87491).

Moreover, the isoquinoline derivative described in the above-mentioned publication (Naunyn-Schmiedeberg's Archives of Pharmacology 385(1) Suppl., R219, 1998) is known to be useful as an agent for the prevention and treatment of brain tissue disorder due to vasospasm (WO97/28130).

However, compounds having Rho kinase inhibitory activity are not reported to be useful for renal diseases.

DISCLOSURE OF THE INVENTION

The present invention aims at solving the above-mentioned problems and provides a novel agent for the prophylaxis or treatment of renal diseases.

In an attempt to solve the above-mentioned problems, the present inventors have conducted intensive studies and found that a compound having a Rho kinase inhibitory activity shows a renal interstitial fibrosis inhibitory action, and therefore, is useful as a prophylactic and therapeutic agent of renal diseases, which resulted in the completion of the present invention.

Accordingly, the present invention provides the following.

(1) An agent for the prophylaxis or treatment of a renal disease, which comprises a compound having a Rho kinase inhibitory activity.

(2) The agent for the prophylaxis or treatment of a renal disease of (1) above, wherein the compound having a Rho kinase inhibitory activity is an amide compound of the following formula (I)

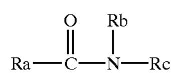

(I)

wherein

Ra is a group of the formula

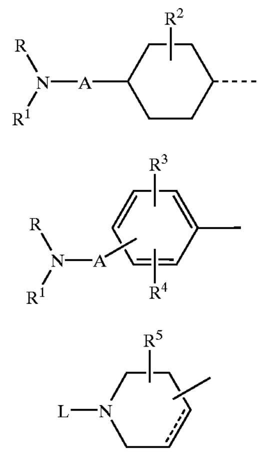

(a)

(b)

(c)

in the formulas (a) and (b),

R is hydrogen, alkyl, or cycloalkyl, cycloalkylalkyl, phenyl or aralkyl, which optionally has a substituent on the ring, or a group of the formula

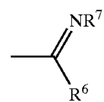

(d)

wherein $R^6$ is hydrogen, alkyl or formula: $—NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

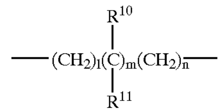

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and 1, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

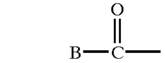

(f)

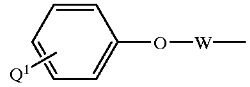

(g)

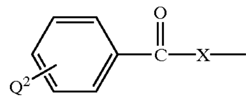

(h)

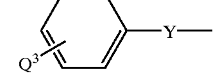

(i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(3) The agent for the prophylaxis or treatment of a renal disease of (1) or (2) above, wherein the compound having a Rho kinase inhibitory activity is an amide compound of the following formula (I')

(I')

$$\mathrm{Ra'}-\overset{\overset{\displaystyle O}{\|}}{C}-\underset{}{\overset{\overset{\displaystyle Rb}{|}}{N}}-\mathrm{Rc}$$

wherein

Ra' is a group of the formula (a')

(b')

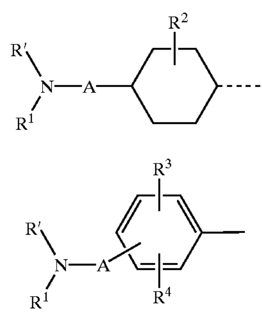

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula (e)

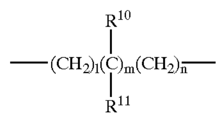

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and 1, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(4) The agent for the prophylaxis or treatment of a renal disease of (1), wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl) benzamide and (R)-(+)-N-(1H-pyrrolo[2,3-b]pyridin-4-yl)-4-(1-aminoethyl)benzamide, and/or a pharmaceutically acceptable acid addition salt thereof, especially (+)-trans-4-(1-aminoethyl)-1-(4-pyridylcarbamoyl)cyclohexane and/or a pharmaceutically acceptable acid addition salt thereof.

(5) The agent for the prophylaxis or treatment of a renal disease of any of (1) to (4) above, wherein the renal disease accompanies renal fibrosis.

(6) The agent for the prophylaxis or treatment of a renal disease of (5) above, wherein the renal disease accompanying renal fibrosis is interstitial renal fibrosis.

(7) A pharmaceutical composition for the prophylaxis or treatment of renal disease, which comprises a compound having a Rho kinase inhibitory activity and a pharmaceutically acceptable carrier.

(8) The pharmaceutical composition for the prophylaxis or treatment of renal disease of (7) above, wherein the compound having a Rho kinase inhibitory activity is an amide compound of the formula (I), an isomer thereof and/or a pharmaceutically acceptable acid addition salt thereof.

(9) The pharmaceutical composition for the prophylaxis or treatment of renal disease of (7) or (8) above, wherein the compound having a Rho kinase inhibitory activity is an amide compound of the formula (I'), an isomer thereof and/or a pharmaceutically acceptable acid addition salt thereof.

(10) The pharmaceutical composition for the prophylaxis or treatment of renal disease of (7) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)-cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof, especially (+)-trans-4-(1-aminoethyl)-1-(4-pyridylcarbamoyl) cyclohexane and/or a pharmaceutically acceptable acid addition salt thereof.

(11) The pharmaceutical composition for the prophylaxis or treatment of renal disease of any of (7) to (10) above, wherein the renal disease accompanies renal fibrosis.

(12) The pharmaceutical composition for the prophylaxis or treatment of renal disease of (11) above, wherein the renal disease accompanying renal fibrosis is interstitial renal fibrosis.

(13) A method of the prophylaxis or treatment of renal disease, which comprises administering a pharmaceutically effective amount of a compound having a Rho kinase inhibitory activity to a patient.

(14) The method of the prophylaxis or treatment of renal disease of (13) above, wherein the compound having a Rho kinase inhibitory activity is an amide compound of the formula (I), an isomer thereof and/or a pharmaceutically acceptable acid addition salt thereof.

(15) The method of the prophylaxis or treatment of renal disease of (13) or (14) above, wherein the compound having a Rho kinase inhibitory activity is an amide compound of the formula (I'), an isomer thereof and/or a pharmaceutically acceptable acid addition salt thereof.

(16) The method of the prophylaxis or treatment of renal disease of (13) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2, 3-b]pyridin-4-yl)-4-(1-aminoethyl)cyclohexanecarboxamide, (R)-(+)-N-(4-pyridyl)-4-(1-aminoethyl) benzamide and (R)-(+)-N-(1H-pyrrolo[2,3-b]pyridin-4-yl)-4-(1-aminoethyl)benzamide, and/or a pharmaceutically acceptable acid addition salt thereof, especially (+)-trans-4-(1-aminoethyl)-1-(4-pyridylcarbamoyl)cyclohexane and/or a pharmaceutically acceptable acid addition salt thereof.

(17) The method of the prophylaxis or treatment of renal disease of any of the above-mentioned (13)–(16), wherein the renal disease accompanies renal fibrosis.

(18) The method of the prophylaxis or treatment of renal disease of (17) above, wherein the renal disease accompanying fibrosis is interstitial renal fibrosis.

(19) Use of a compound having a Rho kinase inhibitory activity for the production of an agent for the prophylaxis or treatment of a renal disease.

(20) The use of (19) above, wherein the compound having a Rho kinase inhibitory activity is an amide compound of the following formula (I), especially formula (I'), an isomer thereof and/or a pharmaceutically acceptable acid addition salt thereof.

(21) The use of (19) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl) cyclohexanecarboxamide, (R)-(+)-N-(4-pyridyl)-4-(1-aminoethyl)benzamide and (R)-(+)-N-(1H-pyrrolo[2,3-b] pyridin-4-yl)-4-(1-aminoethyl)benzamide, and/or a pharmaceutically acceptable acid addition salt thereof, especially (+)-trans-4-(1-aminoethyl)-1-(4-pyridylcarbamoyl) cyclohexane and/or a pharmaceutically acceptable acid addition salt thereof.

(22) The use of any of (19) to (21) above, wherein the renal disease accompanies renal fibrosis.

(23) The use of (22) above, wherein the renal disease accompanying renal fibrosis is interstitial renal fibrosis.

(24) A commercial package comprising a pharmaceutical composition for the prophylaxis or treatment of renal disease of any of (7) to (12) above, and a written matter associated therewith, the written matter stating that the pharmaceutical composition can or should be used for the prophylaxis or treatment of renal disease.

Figure 1:
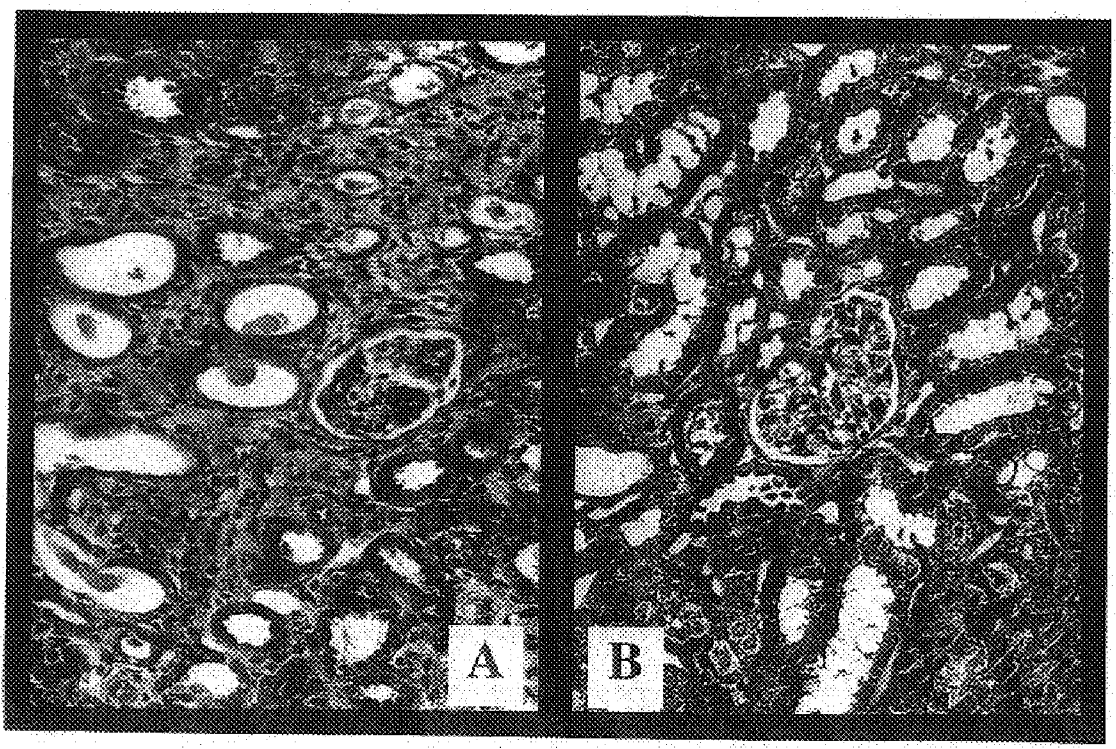
FIG. 1 shows the results (photographs) of Masson trichrome stained kidney specimen of the renal interstitial fibrosis model mouse in Experimental Example 1. FIG. A shows one example of Y-27632 non-administration group and FIG. B shows one example of Y-27632 administration group.

Y-27632: (+)-trans-4-(1-aminoethyl)-1-(4-pyridylcarbamoyl)-cyclohexane 2HCl.1$H_2O$

DETAILED DESCRIPTION OF THE INVENTION

The renal disease in the present invention includes a disease wherein hematuria and proteinuria are developed by various causes, and a disease wherein kidney function becomes low to develop acute or chronic renal failure that requires dialysis as the occasion demands. Examples thereof include progressive renal diseases such as glomerulonephritis, interstitial nephritis, pyelonephritis, glomerulosclerosis, acute tubular necrosis, nephrotic syndrome, pharmaceutical renal disorder, diabetic nephropathy, autoimmune nephropathy and the like, and the disease includes terminal kidney failure and the like, that developed from these progressive renal diseases.

In any progressive renal diseases and terminal kidney failure developed from these diseases, renal fibrosis concomitantly developed and shows a significant disease state. The present invention encompasses any renal disease that accompanies such renal fibrosis. Of the renal diseases, interstitial nephritis, interstitial renal fibrosis and the like mainly caused by renal fibrosis are particularly a preferable target disease in the present invention.

The compound having a Rho kinase inhibitory activity, which is used as an active ingredient in the present invention, may be any as long as it has a Rho kinase inhibitory activity. In the present invention, Rho kinase means serine/threonine kinase activated along with the activation of Rho. For example, ROKα (ROCKII: Leung, T. et al, J. Biol. Chem., 270, 29051–29054, 1995), p160 ROCK (ROKβ, ROCK-I: Ishizaki, T. et al, The EMBO J., 15(8), pp.1885–1893, 1996) and other proteins having a serine/threonine kinase activity are exemplified.

Examples of the compound having a Rho kinase inhibitory activity, which is used in the present invention, include the amide compound, isoquinolinesulfonamide derivative and isoquinoline derivative described in the above-mentioned WO98/06433, WO97/28130 and Naunyn-Schmiedeberg's Archives of Pharmacology 385(1), Suppl., R219 (1998), and vinyl benzene derivative and cinnamic acid derivative described in WO00/57914 and JP-A-2000-44513.

As the aforementioned amide compound, for example, a compound of the above-mentioned formula (I), particularly a compound of the formula (I'), are used. As the aforementioned isoquinolinesulfonamide derivative, hexahydro-1-(5-isoquinolinesulfonyl)-1H-1,4-diazepine hydrochloride [fasudil hydrochloride] and the like are used. As the aforementioned isoquinoline derivative, hexahydro-1-[(4-methyl-5-isoquinolinyl)sulfonyl]-1H-1,4-diazepine dihydrochloride, (S)-(+)-hexahydro-2-methyl-1-[(4-methyl-5-isoquinolinyl)sulfonyl]-1H-1,4-diazepine hydrochloride, hexahydro-7-methyl-1-[(4-methyl-5-isoquinolinyl) sulfonyl]-1H-1,4-diazepine dihydrochloride, hexahydro-5-methyl-1-[(4-methyl-5-isoquinolinyl)sulfonyl]-1H-1,4-diazepine dihydrochloride, hexahydro-2-methyl-1-[(4-methyl-5-isoquinolinyl)sulfonyl]-1H-1,4-diazepine hydrochloride, (R)-(−)-hexahydro-2-methyl-1-[(4-methyl-5-isoquinolinyl)-sulfonyl]-1H-1,4-diazepine hydrochloride, (R)-(+)-hexahydro-5-methyl-1-[(4-methyl-5-isoquinolinyl) sulfonyl]-1H-1,4-diazepine hydrochloride and the like are used.

As the aforementioned vinyl benzene derivative and cinnamic acid derivative, ethacrynic acid, 4-[2-(2,3,4,5,6-pentafluorophenyl)acryloyl]cinnamic acid and the like are mentioned.

It is preferably an amide compound represented by the formula (I), particularly preferably an amide compound represented by the formula (I').

In the present invention, one kind of a compound having a Rho kinase inhibitory activity may be used alone, or, where necessary, several kinds may be concurrently used.

In the present invention, a compound having a Rho kinase inhibitory activity, which is an active ingredient, and other therapeutic agents of renal diseases can be used in combination.

In the present specification, each symbol of the formulas (I) and (I') is defined as follows.

Alkyl at R, R' and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl at R, R' and $R^1$ has 3 to 7 carbon atoms and is exemplified by cyclopropyl, cyclobutyl, cyclopentyl, cyclohexyl, cycloheptyl and the like.

Cycloalkylalkyl at R, R' and $R^1$ is that wherein the cycloalkyl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylhexyl, cyclobutylhexyl, cyclopentylhexyl, cyclohexylhexyl, cycloheptylhexyl and the like.

Aralkyl at R, R' and $R^1$ is that wherein alkyl moiety is alkyl having 1 to 4 carbon atoms and is exemplified by phenylalkyl such as benzyl, 1-phenylethyl, 2-phenylethyl, 3-phenylpropyl, 4-phenylbutyl and the like.

The substituent of optionally substituted cycloalkyl, cycloalkylalkyl, phenyl and aralkyl on the ring at R, R' and $R^1$ is halogen (e.g., chlorine, bromine, fluorine and iodine), alkyl (same as alkyl at R, R' and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl at R, R' and $R^1$) or haloalkyl (alkyl at R, R' and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and $R^1$ or R' and $R^1$ in combination together with the adjacent nitrogen atom, which forms a heterocycle optionally further having, in the ring, oxygen atom, sulfur atom or optionally substituted nitrogen atom is preferably a 5 or 6-membered ring and bonded ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R, R' and $R^1$.

Alkyl at $R^2$ is as defined for R, R' and $R^1$.

Halogen, alkyl, alkoxy and aralkyl at $R^3$ and $R^4$ are as defined for R, R' and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is linear or branched alkyl having 1 to 6 carbon atoms. Examples thereof include methylamino, ethylamino, propylamino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzoyl or the alkanoyl moiety is phenylalkanoyl having 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

Aralkylthio at $R^3$ and $R^4$ is that wherein the alkyl moiety is alkyl having 1 to 4 carbon atoms, which is exemplified by benzylthio, 1-phenylethylthio, 2-phenylethylthio, 3-phenylpropylthio, 4-phenylbutylthio and the like.

Alkoxycarbonyl at $R^3$ and $R^4$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Mono- or di-alkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R, R' and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1$–$C_4$ alkyl, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

Alkyl at $R^6$ is as defined for R, R' and $R^1$; alkyl at $R^8$ and $R^9$ is as defined for R, R' and $R^1$; and aralkyl at $R^8$ and $R^9$ is as defined for R, R' and $R^1$.

Alkyl at $R^7$ is as defined for R, R' and $R^1$ and aralkyl at $R^7$ is as defined for R, R' and $R^1$.

The group formed by $R^6$ and $R^7$ in combination, which forms a heterocycle optionally further having, in the ring, oxygen atom, sulfur atom or optionally substituted nitrogen atom, is exemplified by imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl, nitro, amino, phenyl, aralkyl and the like. As used herein, halogen, alkyl, alkoxy, haloalkyl and aralkyl are as defined for R, R' and $R^1$.

The substituent of the above-mentioned optionally substituted nitrogen atom is exemplified by alkyl, aralkyl, haloalkyl and the like. As used herein, alkyl, aralkyl and haloalkyl are as defined for R, R' and $R^1$.

Hydroxyalkyl at $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like.

Alkyl at $R^{10}$ and $R^{11}$ is as defined for R, R' and $R^1$; haloalkyl and alkoxycarbonyl at $R^{10}$ and $R^{11}$ are as defined for R, R' and $R^1$; aralkyl at $R^{10}$ and $R^{11}$ is as defined for R, R' and $R^1$.

Cycloalkyl formed by $R^{10}$ and $R^{11}$ in combination is the same as cycloalkyl at R, R' and $R^1$.

Alkyl at L is as defined for R, R' and $R^1$.

Aminoalky at L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl at L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

Carbamoylalkyl at L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl at L is linear or branched alkyl having 1 to 6 carbon atoms, which is substituted by phthalimide. Examples-thereof include phthalimidomethyl, 2-phthalimidoethyl, 1-phthalimidoethyl, 3-phthalimidopropyl, 4-phthalimidobutyl, 5-phthalimidopentyl, 6-phthalimidohexyl and the like.

Alkyl at B is as defined for R, R' and $R^1$.

Alkoxy at B is as defined for R, R' and $R^1$.

Aralkyl at B is as defined, for R, R' and $R^1$.

Aralkyloxy at B is as defined for $R^3$ and $R^4$.

Aminoalkyl at B is as defined for L.

Hydroxyalkyl at B is as defined for $R^{10}$ and $R^{11}$.

Alkanoyloxyalkyl at B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl at B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen at $Q^1$, $Q^2$ and $Q^3$ is as defined for R, R' and $R^1$. Aralkyloxy at $Q^1$ and $Q^2$ is as defined for $R^3$ and $R^4$.

Alkoxy at $Q^3$ is as defined for R, R' and $R^1$.

Alkylene at W, X and Y is linear or branched alkylene having 1 to 6 carbon atoms, which is exemplified by methylene, ethylene, trimethylene, propylene, tetramethylene, pentamethylene, hexamethylene and the like.

Alkenylene at Y is linear or branched alkenylene having 2 to 6 carbon atoms, which is exemplified by vinylene, propenylene, butenylene, pentenylene and the like.

Alkyl at Rb is as defined for R, R' and $R^1$.

Aralkyl at Rb is as defined for R, R' and $R^1$.

Aminoalkyl at Rb is as defined for L.

Mono- or dialkylaminoalkyl at Rb is as defined for L.

The nitrogen-containing heterocycle at Rc, when it is a monocyclic ring, is exemplified by pyridine, pyrimidine, pyridazine, triazine, pyrazole, triazole and the like, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrrolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a]pyrimidine, 1H-pyrazolo[4,3-d]pyrimidine and the like), imidazopyrimidine (e.g., imidazo[1,2-a]pyrimidine, 1H-imidazo[4,5-d]pyrimidine and the like), pyrrolotriazine (e.g., pyrrolo[1,2-a]-1,3,5-triazine, pyrrolo[2,1-f]-1,2,4-triazine), pyrazolotriazine (e.g., pyrazolo[1,5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo[5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]pyrimidine, furo[3,2-d]pyrimidine and the like), 2,3-dihydropyrrolopyridine (e.g., 2,3-dihydro-1H-pyrrolo[2,3-b]pyridine, 2,3-dihydro-1H-pyrrolo[3,2-b]pyridine and the like), 2,3-dihydropyrrolopyrimidine (e.g., 2,3-dihydro-1H-pyrrolo[2,3-d]pyrimidine, 2,3-dihydro-1H-pyrrolo[3,2-d]pyrimidine and the like), 5,6,7,8-tetrahydropyrido[2,3-d]pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, mono- or di-alkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R, R' and $R^1$ and exemplified by methylhydrazino, ethylhydrazino, benzylhydrazino and the like.

The compound of the formula (I) is exemplified by the following compounds.

(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) 1-[3-(2-(2-thienylmethyl)phenoxy)-2-hydroxypropyl]-4-(4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine
(9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)piperidine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1-methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyridylcarbamoyl)piperidine
(18) 1-(2-(4-methoxyphenyl)ethyl)-4-(4-pyridylcarbamoyl)-piperidine
(19) 1-(2-(4-methoxyphenyl)ethyl)-4-(2-pyridylcarbamoyl)-piperidine
(20) 1-(2-(4-chlorophenyl)ethyl)-4-(4-pyridylcarbamoyl)-piperidine
(21) 1-diphenylmethyl-4-(2-pyridylcarbamoyl)piperidine
(22) 1-[2-(4-(5-methyl-3-oxo-2,3,4,5-tetrahydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)piperidine
(24) 1-(2-nitrophenyl)-4-(4-pyridylcarbamoyl)piperidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trimethoxybenzoyl)-4-(4-pyridylcarbamoyl)-piperidine
(29) 1-acetyl-4-(4-pyridylcarbamoyl)piperidine
(30) 1-(3-(4-fluorobenzoyl)propyl)-4-(4-pyridylcarbamoyl)-piperidine
(31) 1-(3-(4-fluorobenzoyl)propyl)-4-(2-pyridylcarbamoyl)-piperidine
(32) 1-(1-(4-hydroxybenzoyl)ethyl)-4-(2-pyridylcarbamoyl)-piperidine
(33) 1-(1-(4-benzyloxybenzoyl)ethyl)-4-(2-pyridylcarbamoyl)-piperidine
(34) 1-(2-(4-hydroxyphenoxy)ethyl)-4-(2-pyridylcarbamoyl)-piperidine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)-piperidine
(39) 1-(2-hydroxy-3-phenoxypropyl)-4-(3-pyridylcarbamoyl)-piperidine
(40) 1-(2-hydroxy-3-phenoxypropyl)-4-(2-pyridylcarbamoyl)-piperidine
(41) 1-(2-phenylethyl)-4-[N-(2-pyridyl)-N-(2-(N,N-dimethylamino)ethyl)carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)-piperidine
(44) 4-[N-(2-pyridyl)-N-(2-(N,N-dimethylamino)ethyl)-carbamoyl]piperidine
(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)-piperidine
(48) 1-(6-chloro-2-methylimidazo[1,2-a]pyridine-3-carbonyl)-4-(4-pyridylcarbamoyl)piperidine
(49) 1-(4-nitrobenzyl)-4-(4-pyridylcarbamoyl)piperidine
(50) 1-hexyl-4-(4-pyridylcarbamoyl)piperidine
(51) 1-benzyloxycarbonyl-4-(2-chloro-4-pyridylcarbamoyl)-piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5-di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)-piperidine
(59) 4-(5-nitro-2-pyridylcarbamoyl)piperidine
(60) trans-4-benzyloxycarboxamidomethyl-1-(4-pyridylcarbamoyl)cyclohexane
(61) trans-4-aminomethyl-1-(4-pyridylcarbamoyl)cyclohexane
(62) trans-4-formamidomethyl-1-($^4$-pyridylcarbamoyl)-cyclohexane
(63) trans-4-dimethylaminomethyl-1-(4-pyridylcarbamoyl)-cyclohexane
(64) N-benzylidene-trans-(4-pyridylcarbamoyl)-cyclohexylmethylamine
(65) trans-4-benzylaminomethyl-1-(4-pyridylcarbamoyl)-cyclohexane
(66) trans-4-isopropylaminomethyl-1-(4-pyridylcarbamoyl)-cyclohexane
(67) trans-4-nicotinoylaminomethyl-1-(4-pyridylcarbamoyl)-cyclohexane
(68) trans-4-cyclohexylaminomethyl-1-(4-pyridylcarbamoyl)-cyclohexane
(69) trans-4-benzyloxycarboxamide-1-(4-pyridylcarbamoyl)-cyclohexane

(70) trans-4-amino-1-(4-pyridylcarbamoyl)cyclohexane
(71) trans-4-(1-aminoethyl)-1-(4-pyridylcarbamoyl) cyclohexane
(72) trans-4-aminomethyl-cis-2-methyl-1-(4-pyridylcarbamoyl)-cyclohexane
(73) (+)-trans-4-(1-benzyloxycarboxamidopropyl)-1-cyclohexanecarboxylic acid
(74) (+)-trans-4-(1-benzyloxycarboxamidopropyl)-1-(4-pyridylcarbamoyl)cyclohexane
(75) (−)-trans-4-(1-benzyloxycarboxamidopropyl)-1-(4-pyridylcarbamoyl)cyclohexane
(76) (+)-trans-4-(1-aminopropyl)-1-(4-pyridylcarbamoyl)-cyclohexane
(77) (−)-trans-4-(1-aminopropyl)-1-(4-pyridylcarbamoyl)-cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)-cyclohexane
(81) (−)-trans-4-(1-aminoethyl)-1-(4-pyridylcarbamoyl)-cyclohexane
(82) trans-4-(4-chlorobenzoyl)aminomethyl-1-(4-pyridylcarbamoyl)cyclohexane
(83) trans-4-aminomethyl-1-(2-pyridylcarbamoyl) cyclohexane
(84) trans-4-benzyloxycarboxamidomethyl-1-(2-pyridylcarbamoyl)cyclohexane
(85) trans-4-methylaminomethyl-1-(4-pyridylcarbamoyl)-cyclohexane
(86) trans-4-(N-benzyl-N-methylamino)methyl-1-(4-pyridylcarbamoyl)cyclohexane
(87) trans-4-aminomethyl-1-(3-pyridylcarbamoyl) cyclohexane
(88) trans-4-aminomethyl-1-[(3-hydroxy-2-pyridyl) carbamoyl]-cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)-cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)-cyclohexane
(94) 4-(trans-4-benzyloxycarboxamidomethylcyclohexyl-carbonyl)amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)-cyclohexane
(97) trans-4-(1-benzyloxycarboxamidoethyl)-1-(4-pyridylcarbamoyl)cyclohexane
(98) trans-4-(1-amino-1-methylethyl)-1-(4-pyridylcarbamoyl)-cyclohexane
(99) trans-4-(2-aminoethyl)-1-(4-pyridylcarbamoyl) cyclohexane
(100) trans-4-(2-amino-1-methylethyl)-1-(4-pyridylcarbamoyl)-cyclohexane
(101) trans-4-(1-aminopropyl)-1-(4-pyridylcarbamoyl)-cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethylcyclohexanecarboxamide
(108) trans-N-(1H-pyrrolo[2,3-b]pyridin-4-yl)-4-aminomethylcyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl)-4-(1-amino-1-methylethyl)cyclohexanecarboxamide
(111) trans-N-(1H-pyrazolo[3,4-b]pyridin-4-yl)-4-aminomethylcyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)-cyclohexanecarboxamide
(115) trans-N-(1H-pyrazolo[3,4-d]pyrimidin-4-yl)-4-aminomethylcyclohexanecarboxamide
(116) (+)-trans-N-(1H-pyrazolo[3,4-d]pyrimidin-4-yl)-4-(1-aminoethyl)cyclohexanecarboxamide
(117) trans-N-(1H-pyrazolo[3,4-d]pyrimidin-4-yl)-4-(1-amino-1-methylethyl)cyclohexanecarboxamide
(118) trans-N-(4-pyrimidinyl)-4-aminomethylcyclohexanecarboxamide
(119) trans-N-(3-amino-4-pyridyl)-4-aminomethylcyclohexanecarboxamide
(120) trans-N-(7H-imidazo[4,5-d]pyrimidin-6-yl)-4-aminomethylcyclohexanecarboxamide
(121) trans-N-(3H-1,2,3-triazolo[4,5-d]-pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethylcyclohexanecarboxamide
(124) trans-N-(1H-pyrazolo[3,4-b]pyridin-4-yl)-4-aminomethylcyclohexanecarboxamide
(125) trans-N-(4-pyridazinyl)-4-aminomethylcyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethylcyclohexanecarboxamide
(128) trans-N-(thieno[2,3-d]pyrimidin-4-yl)-4-aminomethylcyclohexanecarboxamide
(129) trans-N-(5-methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(1-amino-1-methylethyl)cyclohexanecarboxamide
(132) trans-N-(2-(1-pyrrolidinyl)-4-pyridyl)-4-aminomethylcyclohexanecarboxamide
(133) trans-N-(2,6-diamino-4-pyrimidyl)-4-aminomethylcyclohexanecarboxamide
(134) (+)-trans-N-(7-methyl-1,8-naphthyridin-4-yl)-4-(1-aminoethyl)cyclohexanecarboxamide
(135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide (138) trans-N-(2-azide-4-pyridyl)-4-aminomethylcyclohexanecarboxamide
(139) trans-N-(2,3-dihydro-1H-pyrrolo[2,3-b]pyridin-4-yl)-4-aminomethylcyclohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethylcyclohexanecarboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidinomethylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)cyclohexanecarboxamide
(151) trans-N-(1H-pyrrolo[2,3-b]pyridin-4-yl)-4-(3-phenylguanidinomethyl)cyclohexanecarboxamide
(152) trans-N-(1H-pyrrolo[2,3-b]pyridin-4-yl)-4-(3-propylguanidinomethyl)cyclohexanecarboxamide
(153) trans-N-(1H-pyrrolo[2,3-b]pyridin-4-yl)-4-(3-octylguanidinomethyl)cyclohexanecarboxamide
(154) trans-N-(1-benzyloxymethylpyrrolo[2,3-b]pyridin-4-yl)-4-(2-benzyl-3-ethylguanidinomethyl)cyclohexanecarboxamide
(155) trans-N-(1H-pyrrolo[2,3-b]pyridin-4-yl)-4-(imidazol-2-yl)aminomethylcyclohexanecarboxamide
(156) trans-N-(1H-pyrrolo[2,3-b]pyridin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pyridyl)-4-(1-aminoethyl)-3-nitrobenzamide
(162) (R)-(−)-N-(4-pyridyl)-3-amino-4-(1-aminoethyl)benzamide
(163) (R)-(+)-N-(4-pyridyl)-4-(1-aminoethyl)-3-chlorobenzamide
(164) N-(4-pyridyl)-3-aminomethylbenzamide
(165) (R)-(+)-N-(1H-pyrrolo[2,3-b]pyridin-4-yl)-4-(1-aminoethyl)benzamide
(166) (R)-(+)-N-(1H-pyrazolo[3,4-b]pyridin-4-yl)-4-(1-aminoethyl)benzamide
(167) N-(1H-pyrazolo[3,4-b]pyridin-4-yl)-4-guanidinomethylbenzamide
(168) N-(4-pyridyl)-4-guanidinomethylbenzamide
(169) (R)-(+)-N-(4-pyridyl)-4-(1-aminoethyl)-3-fluorobenzamide
(170) N-(4-pyridyl)-4-aminomethylbenzamide
(171) N-(4-pyridyl)-4-aminomethyl-2-hydroxybenzamide
(172) N-(4-pyridyl)-4-(2-aminoethyl)benzamide
(173) N-(4-pyridyl)-4-aminomethyl-3-nitrobenzamide
(174) N-(4-pyridyl)-3amino-4-aminomethylbenzamide
(175) (S)-(−)-N-(4-pyridyl)-4-(1-aminoethyl)benzamide
(176) (S)-(−)-N-(4-pyridyl)-2-(1-aminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzamide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitrobenzamide
(186) (R)-N-(1H-pyrazolo[3,4-b]pyridin-4-yl)-4-(1-guanidinoethyl)-3-nitrobenzamide
(187) (R)-N-(1H-pyrazolo[3,4-b]pyridin-4-yl)-4-(1-aminoethyl)-2-nitrobenzamide
(188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4-piperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-piperidinecarboxamide
(199) N-(1H-pyrrolo[2,3-b]pyridin-4-yl)-1-amidino-4-piperidinecarboxamide
(200) N-(1H-pyrrolo[2,3-b]pyridin-4-yl)-1-(3-phenylpropyl)-4-piperidinecarboxamide
(201) N-(1H-pyrrolo[2,3-b]pyridin-4-yl)-1-benzyl-4-piperidinecarboxamide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide
(204) N-(1H-pyrrolo[2,3-b]pyridin-4-yl)-4-(1-amino-1-methylethyl)benzamide Preferred are compounds (80), (109), (110), (112), (115), (142), (143), (144), (145), (153), (157), (163), (165), (166) and (179).

The compound having a Rho kinase inhibitory activity may be a pharmaceutically acceptable acid addition salt, wherein the acid is exemplified by inorganic acid such as hydrochloric acid, hydrobromic acid, sulfuric acid and the like, and organic acid such as methanesulfonic acid, fumaric acid, maleic acid, mandelic acid, citric acid, tartaric acid, salicylic acid and the like. A compound having a carboxyl group can be converted to a salt with a metal such as sodium, potassium, calcium, magnesium, aluminum and the like, a salt with an amino acid such as lysine and the like. Further, monohydrate, dihydrate, ½ hydrate, ⅓ hydrate, ¼ hydrate, ⅔ hydrate, 3/2 hydrate, 6/5 hydrate and the like are encompassed in the present invention.

The compound of the formula (I) can be synthesized by a method described in, for example, JP-A-62-89679, JP-A-3-218356, JP-A-5-194401, JP-A-6-41080, WO95/28387, WO98/06433 and the like.

When the above-mentioned compound having a Rho kinase inhibitory activity has an optical isomer, its racemate or cis-trans isomers, all of them can be used in the present invention. These isomers can be isolated by a conventional method or can be produced using starting materials of the isomers.

When a compound having a Rho kinase inhibitory activity is used as a pharmaceutical agent, particularly as a pharmaceutical agent for the prophylaxis or treatment of renal diseases of the present invention, a pharmaceutical composition for the prophylaxis or treatment of renal diseases, it is formulated into a general pharmaceutical preparation.

For example, the compound having a Rho kinase inhibitory activity is mixed with a pharmaceutically acceptable carrier (e.g., excipient, binder, disintegrator, corrective, corrigent, emulsifier, diluent, solubilizer and the like) to give a pharmaceutical composition or a pharmaceutical preparation in the form of tablet, pill, powder, granule, capsule, troche, syrup, liquid, emulsion, suspension, injection (e.g., liquid, suspension and the like), suppository, inhalant, percutaneous absorber, eye drop, eye ointment and the like in the form suitable for oral or parenteral preparation.

When preparing a solid preparation, additives such as sucrose, lactose, cellulose sugar, D-mannitol, maltitol, dextran, starches, agar, arginates, chitins, chitosans, pectines, tragacanth gum, gum arabic, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethyleneglycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid paraffin and-the like), wax (e.g., jojoba oil, carnauba wax, bee wax and the like), partly or entirely synthesized glycerol fatty acid esters (e.g., lauric acid, myristic acid, palmitic acid and the like), and the like are used. Examples of commercially available products of these include Witepsol (manufactured by Dynamitnovel Ltd.), Farmazol (manufactured by NOF Corporation) and the like.

When preparing a liquid preparation, an additive, such as sodium chloride, glucose, sorbitol, glycerol, olive oil, propylene glycol, ethyl alcohol and the like, is used. When preparing an injection, a sterile aqueous solution such as physiological saline, isotonic solution, oily solution (e.g., sesame oil and soybean oil) and the like are used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The eye drop can appropriately contain various additives such as buffer (borate buffer, acetate buffer, carbonate buffer and the like are preferable for reducing irritation), isotonicity agent, solubilizer, preservative, thickener, chelating agent, pH adjusting agent (generally, pH is preferably adjusted to about 6–8.5) and aromatic.

The dose of the active ingredient of these preparations, is 0.1–100 wt %, suitably 1–50 wt %, of the preparation. While the dose varies depending on the symptom, body weight, age and the like of patients, it is generally about 1–500 mg a day for an adult, which is administered once to several times a day.

EXAMPLES

The present invention is explained in detail by referring to formulation examples and pharmacological action. The present invention is not limited in any way by the examples.

In the following Formulation Examples and Experimental Examples, (+)-trans-4-(1-aminoethyl)-1-(4-pyridylcarbamoyl)cyclohexane 2HCl.1$H_2O$ (Y-27632), which is a compound having a Rho kinase inhibitory activity, was used.

Formulation Example 1

Tablet

| | |
|---|---|
| Compound of the present invention (Y-27632) | 10.0 mg |
| Lactose | 50.0 mg |
| Cornstarch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention (Y-27632), lactose, cornstarch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added. Using a φ7 mm punch, tablets weighing 120 mg per tablet were prepared.

Formulation Example 2

Capsules

| | |
|---|---|
| Compound of the present invention (Y-27632) | 10.0 mg |
| Lactose | 70.0 mg |
| Cornstarch | 35.0 mg |
| Polyvinylpyrrolidone K30 | 2.0 mg |
| Talc | 2.7 mg |
| Magnesium stearate | 0.3 mg |
| | 120.0 mg |

The compound of the present invention, lactose and cornstarch were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in a hard capsule (No. 4) to give a capsule weighing 120 mg.

The pharmacological action of the pharmaceutical agent of the present invention is explained in the following by referring to Experimental Example.

Experimental Example 1

Action in Renal Interstitial Fibrosis Model Mice Due to Unilateral Ureteral Ligation Method Unilateral ureteral ligation mice were prepared according to the reported method (Kidney Int. 54, 110–119, (1998)). Male BL6/C3H F1 mice (6-week-old, body weight 25 g–30 g) were anesthetized with pentobarbital and subjected to median incision. Thereafter, left ureter was detached and ligated at two points with silk thread. Two models were prepared, and 10 mg/kg of Y-27632 was orally administered (administration with drinking water) to one group for consecutive days from 2 days prior to the operation. Ten days postoperation, the kidney on the ureter ligation side was removed, fixed with 4% paraformaldehyde and prepared into specimen, for staining, which were subjected to Masson trichrome staining. The level of renal interstitial fibrosis was calculated by image analysis of the area ratio (interstitium cortex area ratio:%) of the portion stained blue (fibrosis) relative to the entire sight. (Results)

The images of Masson trichrome staining are shown in FIG. 1 and the results of image analysis are shown in Table 1.

TABLE 1

| | Area ratio of interstitium cortex (Fibrosis): % (average value ± SD) |
|---|---|
| Y-27632 non-administration group (n = 5) | 18.1 ± 6.58 |
| Y-27632 administration group (n = 4) | 7.31 ± 3.11** |

**$p < 0.01$ (t-test)

In the Y-27632 non-administration group (FIG. 1A), the portion stained blue was found. When Y-27632 was administered (FIG. 1B), a stained portion was scarcely detected. From these results, it is clear that the administration of Y-27632 significantly suppressed the level of renal interstitial fibrosis (Table 1).

Industrial Applicability

From the above-mentioned Formulation Examples and Experimental Example and other pharmacological tests, a compound having a Rho kinase inhibitory activity is useful as an agent for the prophylaxis or treatment of renal diseases. Particularly from the above-mentioned Experimental Example, a compound having a Rho kinase inhibitory activity shows a renal interstitial fibrosis inhibitory action in renal interstitial fibrosis model mice.

This application is based on a patent application No. 097258/2000 filed in Japan, the content of which is hereby incorporated by reference.

What is claimed is:

1. A method for the prophylaxis or treatment of renal disease which accompanies renal fibrosis, which comprises administering a pharmaceutically effective amount of a compound having a Rho kinase inhibitory activity to a patient in need thereof.

2. The method of claim 1, wherein the compound having a Rho kinase inhibitory activity is an amide compound of the formula (I), (I)

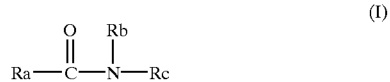

wherein

Ra is a group of the formula (a)

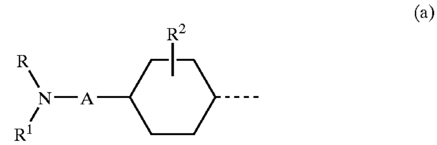

(b)

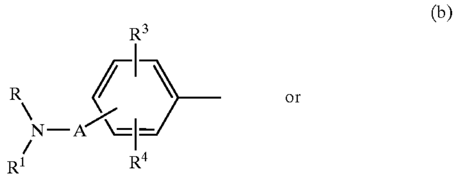

or (c)

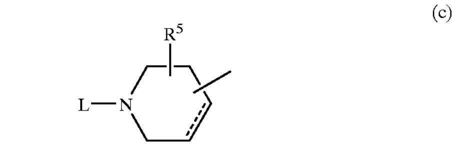

in the formulas (a) and (b),

R is hydrogen, alkyl, or cycloalkyl, cycloalkylalkyl, phenyl or aralkyl, which optionally has a substituent on the ring, or a group of the formula (d)

$$-C(=NR^7)R^6$$

wherein $R^6$ is hydrogen, alkyl or formula: $—NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula (e)

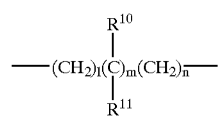

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurftiryl, carbamoylalkyl, phthalimidoalkyl, amidino or a group of the formula (f)

(g)

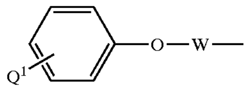

(h)

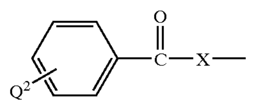

or (i)

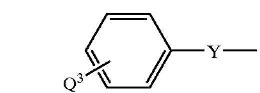

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3 -oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof or a pharmaceutically acceptable acid addition salt thereof.

3. The method of claim 1 or 2, wherein the compound having a Rho kinase inhibitory activity is an amide compound of the formula (I'), (I')

wherein

Ra' is a group of the formula (a')

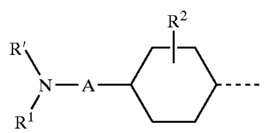

or (b')

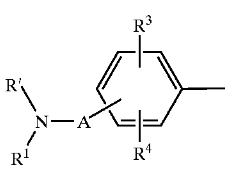

wherein

R' is hydrogen, alkyl, cycloalkyl, cycloalkylalkyl, phenyl or aralkyl, which optionally has a substituent on the ring, $R^1$ is hydrogen, alkyl, cycloalkyl, cycloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula (e)

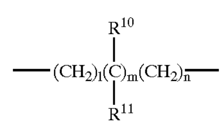

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl, and Rc is an optionally substituted heterocycle containing nitrogen, an isomer thereof or a pharmaceutically acceptable acid addition salt thereof.

4. The method of claim 1, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrro[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl) benzamide, or a pharmaceutically acceptable acid addition salt thereof.

5. The method of claim 1, wherein the compound having a Rho kinase inhibitory activity is (+)-trans-4-(1-aminoethyl)-1-(4-pyridylcarbamoyl)cyclohexane or a pharmaceutically acceptable acid addition salt thereof.

6. The method of claim 1 or 2, wherein the renal disease accompanying renal fibrosis is interstitial renal fibrosis.

* * * * *